United States Patent [19]
Romieu et al.

[11] Patent Number: 5,465,609
[45] Date of Patent: Nov. 14, 1995

[54] APPARATUS FOR STUDY OF GAS MIGRATION IN CEMENT SLAG

[75] Inventors: Jacques Romieu, Bailly; Didier Degouy, Houilles; Philippe Parigot, Chevreuse; Michel Hourcard, Paris, all of France

[73] Assignee: Total, Puteuax, France

[21] Appl. No.: 257,091

[22] Filed: Jun. 7, 1994

[30] Foreign Application Priority Data

Jun. 7, 1993 [FR] France .................................. 93 06768

[51] Int. Cl.$^6$ .................................. G01N 15/08
[52] U.S. Cl. .................................. 73/38; 73/64.41
[58] Field of Search .................... 73/19.01, 19.1, 73/61.43, 38, 61.63, 61.68, 61.71, 64.41

[56] References Cited

U.S. PATENT DOCUMENTS

| | | | |
|---|---|---|---|
| 3,981,202 | 9/1976 | Spangle | 73/438 |
| 4,333,764 | 6/1982 | Richardson | 106/671 |
| 4,933,031 | 6/1990 | Blomberg et al. | 106/672 |

FOREIGN PATENT DOCUMENTS 302604  1/1955  Switzerland.

*Primary Examiner*—Hezron E. Williams
*Assistant Examiner*—Michael J. Brock
*Attorney, Agent, or Firm*—Sughrue, Mion, Zinn, Macpeak and Seas

[57] ABSTRACT

An apparatus for studying the migration of a gas in a cement slag comprises a cell 21 filled at least partially with a slag 22 to be used during the cementation of a well pipe. A first strainer 23 made of a sintered material which simulates a formation is disposed below a second strainer 24 made of a sintered material and connected to a gas-detection apparatus, the levels at which the two strainers are positioned being such that they are embedded in the slag being studied. A pressurized gas source 27 is connected to the first strainer, and to a tank 28 partially filled with water 29, the water-gas interface being located at a level lower than that of the first strainer 23. A line 30 is connected between the bottom of the tank and the upper part of the cell, above the upper level of the slag 22, and actual formation conditions can be simulated by suitably adjusting the vertical height H1 between the water-slag interface in the cell and the water-gas interface in the tank.

4 Claims, 3 Drawing Sheets

APPARATUS FOR STUDY OF GAS MIGRATION IN CEMENT SLAG

BACKGROUND OF THE INVENTION

This invention relates to an apparatus for the analysis of the migration of a gas in a cement slag. More specifically, the invention concerns an apparatus of this kind that can be used in the laboratory for studying a cement slag intended for the cementation of a pipe in a well.

It is known that, when a well is drilled in a soil formation, the pressure exerted by the fluids contained in the permeable rock (i.e., water, petroleum, and especially gas) is controlled and counterbalanced by the hydrostatic pressure generated by a column of mud injected into the well. The density of the drilling mud is regulated so as to exert an excess pressure on the fluids within the formation, to thus prevent them from flowing into the well.

As the drilling progresses, metal tubes are placed in succession in the well, and, at the end of the drilling process, cementation of the space separating the pipe from the formation provides the mechanical strength of the entire assembly, and, in particular, fluid-tightness between the pools through which the well passes, and between these pools and the surface.

Satisfactory fluid-tightness must be achieved during and after the cementing operations; that is, both when the cement slag, still in the liquid state, is put in place and during the cement-hardening phase, or, thereafter, during subsequent use of the well. As the liquid slag is being put in place, the pressures generated can be monitored by studying the losses of head during the slag flow, thereby ensuring the fluid-tightness of the well. Once the cement has hardened, its low level of permeability proves sufficient to prevent fluid flow, provided, of course, that this permeability has not been irreversibly impaired by the passage of gas as the cement hardens.

The critical cementation period thus occurs when the cement is hardening. This period may last several hours, during which complex phenomena, which must be taken into account during any preliminary laboratory study, may take place. These phenomena, which disrupt the monitoring of the hydrostatic pressure of the slag column, relate in particular to:

the sedimentation of the constituents of the cement slag;

the thixotropy resulting from the addition of viscosity additives to the slag;

the dissolution in water of grains of cement and the crystallization thereof;

the shrinkage of the cement slag; and the filtration effect exerted by the well wall on the slag.

The effects of these various phenomena should be studied in the laboratory before any cementation operation, since they directly affect the control of the hydrostatic pressure generated by a column of slag during the cement-hardening phase. They will be analyzed below in greater detail. It will be remembered that, for greater clarity, it is normal state-of-the-art practice to express pressure as "equivalent density" d, the baseline density 1 being that of water. An equivalent density of 1.9 corresponds to normal cement slag, and an equivalent density of 1.6 is an average value for a fluid reservoir. The limiting values are 0.9 and 2.2.

A cement slag is a suspension in water of cement particles and of various additives, the effect of which can be overlooked during a first approach. This suspension is stable when it circulates, but undergoes sedimentation when at rest, after it has been injected into the well. It is highly concentrated and, as soon as sedimentation begins, the cement grains enter into contact with each other. These grains support reciprocally their own weight, and the continuous phase gradually becomes the water in the suspension. There is, consequently, a gradual fall of the hydrostatic pressure generated by the slag column, from that of the initial slag (d=1.9) to that of water (d=1), whose equivalent density represents the theoretical limit.

This phenomenon can be confirmed in a column measuring several meters in height containing a silica suspension, in order to avoid the cement-hardening phenomena. A slow decrease of the hydrostatic pressure is in fact noted. Use is made of additives in normal fashion to increase the viscosity of the suspension fluid, so as to slow sedimentation. Viscosity-increasing additives form thixotrope gels, leading to the fact that the shearing threshold brought to bear on the wall of the well and the surface of the pipe gradually increases as a function of the resting time, and does not allow perfect transmission of pressure. At most, when this threshold increases sufficiently, it can counterbalance the hydrostatic pressure. This is, in fact, what is found when thixotropy is supplemented by an increased mechanical strength of the cement at the time it actually hardens.

Moreover, it is known that the cement grains are gradually dissolved in water, and that when the solution becomes saturated, crystallization occurs. At that time, an increasingly rigid lattice of crystalline fibers is formed. As is the case with sedimentation, this lattice is self-supporting; hydrostatic pressure is then generated solely by the liquid phase, for as long as the permeability of the lattice is sufficient. This lattice also increases the rigidity of the slag, and can, furthermore, reduce the transmission of pressure, if permeability is destroyed.

In addition, a cement slag exhibits a shrinkage of approximately 4 to 5% during hardening. This shrinkage results from the fact that the free water in the suspension occupies a greater volume than does the water associated with the crystal lattice. The hardening of the slag thus causes a reduction of the volume filled by the water. This phenomenon may occur in two different ways:

(1) If the cement sample is subjected to a containment pressure (external pressure greater than the internal pressure), shrinkage is external and gives rise to a reduction of the total volume of the sample. In consequence, there may occur in a horizontal plane the formation of a ring-shaped micro-space between the cement and the soil formation, and/or between the cement and the pipe, and thus, a loss of fluid-tightness. Along a vertical axis, this shrinkage causes a shift of the slag column or, more generally, a decrease of the pressure, when this shift is impeded by the other effects described above.

(2) If the same specimen is subjected to equal pressure (equality of internal and external pressure), shrinkage is then internal, thereby giving increased porosity and a reduction of the pressure of the interstitial fluids. This internal shrinkage explains why the hydrostatic pressure generated by a slag column can fall well below the hydrostatic pressure of a single column of water.

In practice, by virtue of the variations in, and poor transmission of, the hydrostatic pressures, internal and external shrinkage occur simultaneously. This situation thus requires that, during trials in the laboratory, the pressures generated be rigorously monitored.

Lastly, a final phenomenon to be considered arises from the fact that, in the presence of a porous, permeable reservoir, the water/cement suspension tends to filter off, the water from the suspension penetrating into the suspension and the slag drying out at the wall. The dried cement cannot, of course, undergo proper hardening, since its properties have deteriorated; in particular, its permeability is raised, thereby allowing gas to flow into the cement matrix.

Laboratory simulation of the permeable formation and of the differential pressure exerted thus takes on great importance, and the devices used for that purpose must minimize disruption of the measurements made caused by the volume of filtered water (filtrate) during the test.

All of the phenomena mentioned above must be considered with regard to the laboratory devices designed to test cementation. To this end, various test cells have previously been suggested. One of these cells, as shown in FIG. 1, is a conventional apparatus in service since about 1986. It comprises two identical cells 1 and 2, joined in their upper portions by a line 3 incorporating, in a by-pass configuration, a device 4 capable of guaranteeing continuous escape of the fluid flowing in the line 3.

The base of the cell 1 is connected by a line 5 to a buffer chamber 6 containing water 7, this chamber being fed through its upper part with helium pressurized to 30 bars ($30 \times 10^5$ pascals) coming from a tank 8. A piston 9 provided in the cell 1 separates the water 7 fed from the tank 6 from a slag sample 10 to be tested.

A specimen 11 of permeable rock taken from the formation in which cementation is to take place is housed on the bottom of cell 2. This specimen 11 is separated in water-tight fashion from the lateral wall of the cell 1 by fluid-tight systems, symbolized by a joint 12. A line 13 located at the base of cell 2 allows the filtrate to be collected at point 14. This line 13 is connected to a line 15, which is connected in turn to a tank 16 containing gas pressurized to 10 bars ($10 \times 10^5$ pascals), the rock specimen 11 thus simulating a permeable reservoir with a pressure of 10 bars ($10 \times 10^5$ pascals). The slag 10 to be tested is placed above the specimen 11, and above this slag is positioned a water buffer 7 in a configuration similar to that in tank 1.

A strainer 17 made of a sintered material is embedded in the slag 10 in cell 2, in order to detect the migration into the matrix of the gas issuing from the tank 16 through the cement 10. This strainer is connected to a line 18 making it possible to collect the filtrate at point 19. The filtrate volume is measured based on the weighed quantity either through the rock specimen 11 or through the strainer 17.

The two slag specimens 10 are placed in cells 1 and 2 immediately after their fabrication. The pressurized helium from the tank 8 pushes back the piston 9 which, because of the escape of water at 4, slowly shifts the slag in cell 1. When the cement begins to harden, the movement of the piston 9 and of the slag is frozen, and the pressure exerted by the helium is no longer transmitted from cell 1 to cell 2. The escape of water at 4 then ensures a gradual decrease of the pressure in cell 2. This apparatus can thus function entirely automatically, without being acted upon from the outside. The flow rate of the escape at 4 need only be adjusted at the beginning of the test.

A major disadvantage of the apparatus lies in the fact that the pressures generated ($10 \times 10^5$ pascals on the bottom of cell 2, and $30 \times 10^5$ pascals at the top) are not consistent with the pressure actually exerted by the slag column in the cell, whose height is normally about 50 cm. A second disadvantage of this apparatus, of a radically incapacitating nature, is that the pressure in the left-hand cell does not decrease when the piston 9 is frozen, i.e., when the cement has practically hardened in the two cells. Even if the gas pressure ($10 \times 10^5$ pascals) at the base of the cell is then much higher than the hydrostatic pressure of the cement, this phenomenon occurs too late to allow the passage of the gas.

FIG. 2 illustrates the curves recorded as a function of time, using this apparatus. Curve $C_1$ illustrates temperature variations, and curve $C_2$, slag pressure variations. Curves $C_3$ and $C_4$ correspond to the pressure of the tank and of the detection cell. It can be seen that the pressure of the slag (curve $C_2$) falls only after the slag temperature, which indicates the hardening thereof, has begun to rise. The constancy of the pressures of the tank and the detection cell confirms the gas-impermeability of the unit.

One could, quite naturally, contemplate solving certain difficulties exhibited by this conventional apparatus by using cells of substantial height. However, in addition to the fact that these apparatuses are bulky, they require the use of large volumes of slag, so that the procedure for fabrication of the slag, standardized by the American Petroleum Institute, cannot be adhered to, and the slags studied do not have properties that can be duplicated. Moreover, using the large-size cells, it is not possible to conduct tests in the high-temperature ovens in which the cell must be placed.

SUMMARY OF THE INVENTION

The present invention provides an apparatus which overcomes these disadvantages, by virtue of the fact that it uses a small-size cell and that, during use, this cell makes it possible to simulate a decline of hydrostatic pressure in the slag during hardening, and to record any potential migration of gas.

To that end, the invention is directed to an apparatus for studying the migration of gases during cementation of a pipe in a well, and comprises:

a cell capable of being filled at least partially with the slag to be used during cementation;

in this cell and at a first level, a first strainer made of a sintered material which simulates a formation; and, at a second level higher than the first, a second strainer made of a sintered material and connected to a gas-detection apparatus, the levels at which the two strainers are positioned being such that they are embedded in the slag being studied;

a pressurized gas source connected, first, to the first strainer, and second, to a tank partially filled with water, the water-gas interface in this reservoir being located at a level lower than that of the first strainer; and a connection between the part of the tank filled with water and the upper part of the cell, above the upper level of the slag.

DETAILED DESCRIPTION OF THE PREFERRED EMBODIMENT

The following detailed description will show that the differential pressure between the interior and exterior of the first, or injection, strainer, i.e., the pressure difference between the gas source and slag, may be regulated simply by adjusting the distance separating the water-gas interface in the tank from the water-slag interface in the cell; and that an equivalent density corresponding to the fluid pressure of the formation simulated by the first strainer is proportional to this height. By changing this height, that is, by adjusting the height of the water-gas interface in the tank, it is possible to adjust this pressure in a particularly simple fashion for an entire range of equivalent densities of geographical formation fluids.

During the cement-hardening process, the hydrostatic pressure of the fluid diminishes on the outside of the first strainer (injection strainer), and the gas injected into this strainer can potentially migrate into the slag when the pressure on the inside of the strainer is greater than that obtaining on the outside. This migration can then be detected by the second, or detection, strainer. The apparatus according to the invention thus constitutes an especially simple system for laboratory testing of the conditions governing cementation of a pipe in a well.

The strainers are advantageously composed of hollow bodies, e.g., cylindrical in form, made of a sintered material having a stable permeability. Because these strainers are immersed in the slag, the gas migration detected by the second, or detection, strainer occurs necessarily in the matrix.

Figure 1:
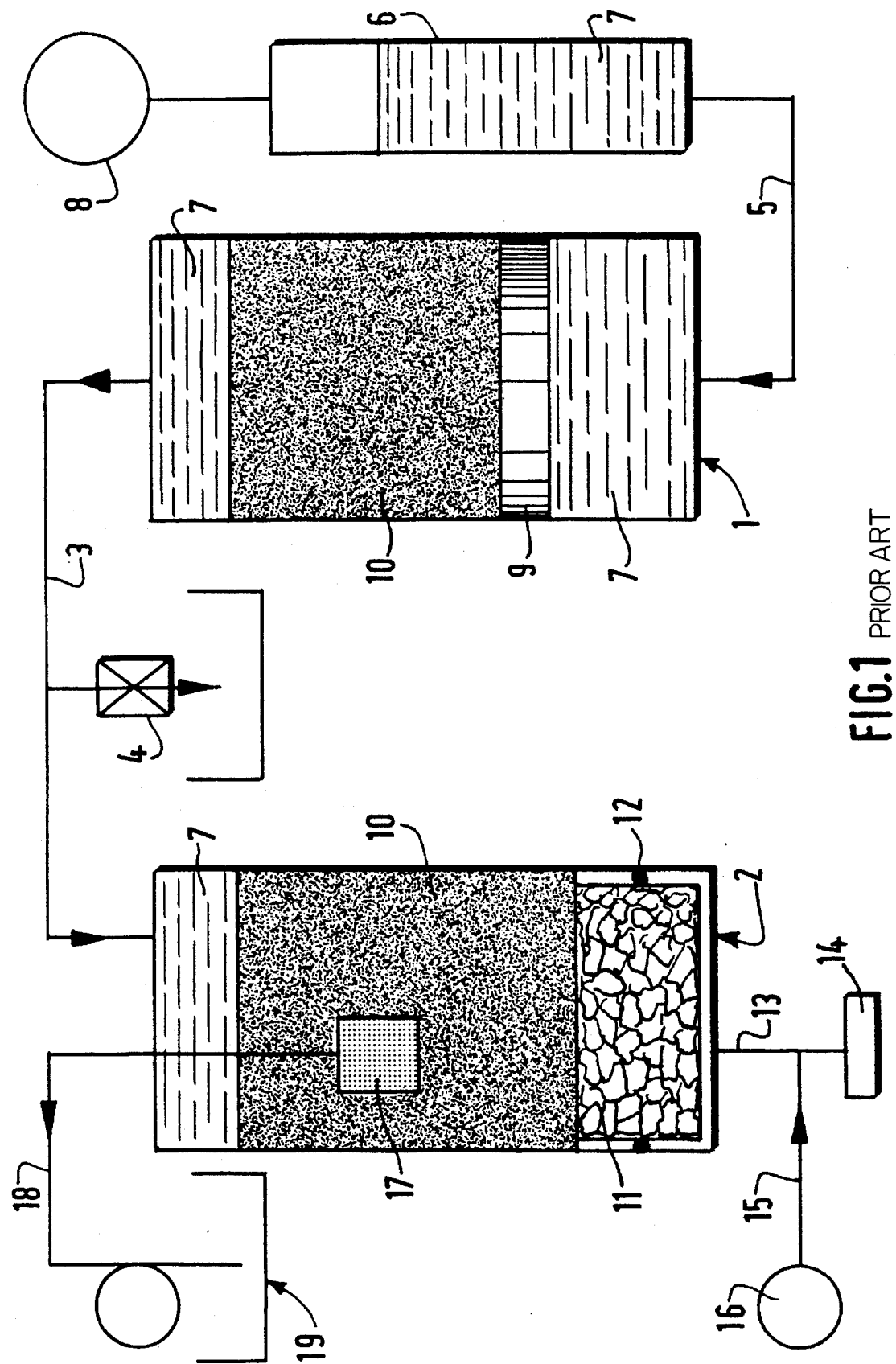
FIG. 1 is a graphic representation of an apparatus according to the prior art, used for the laboratory study of the cementation of a pipe in a well.
Figure 2:
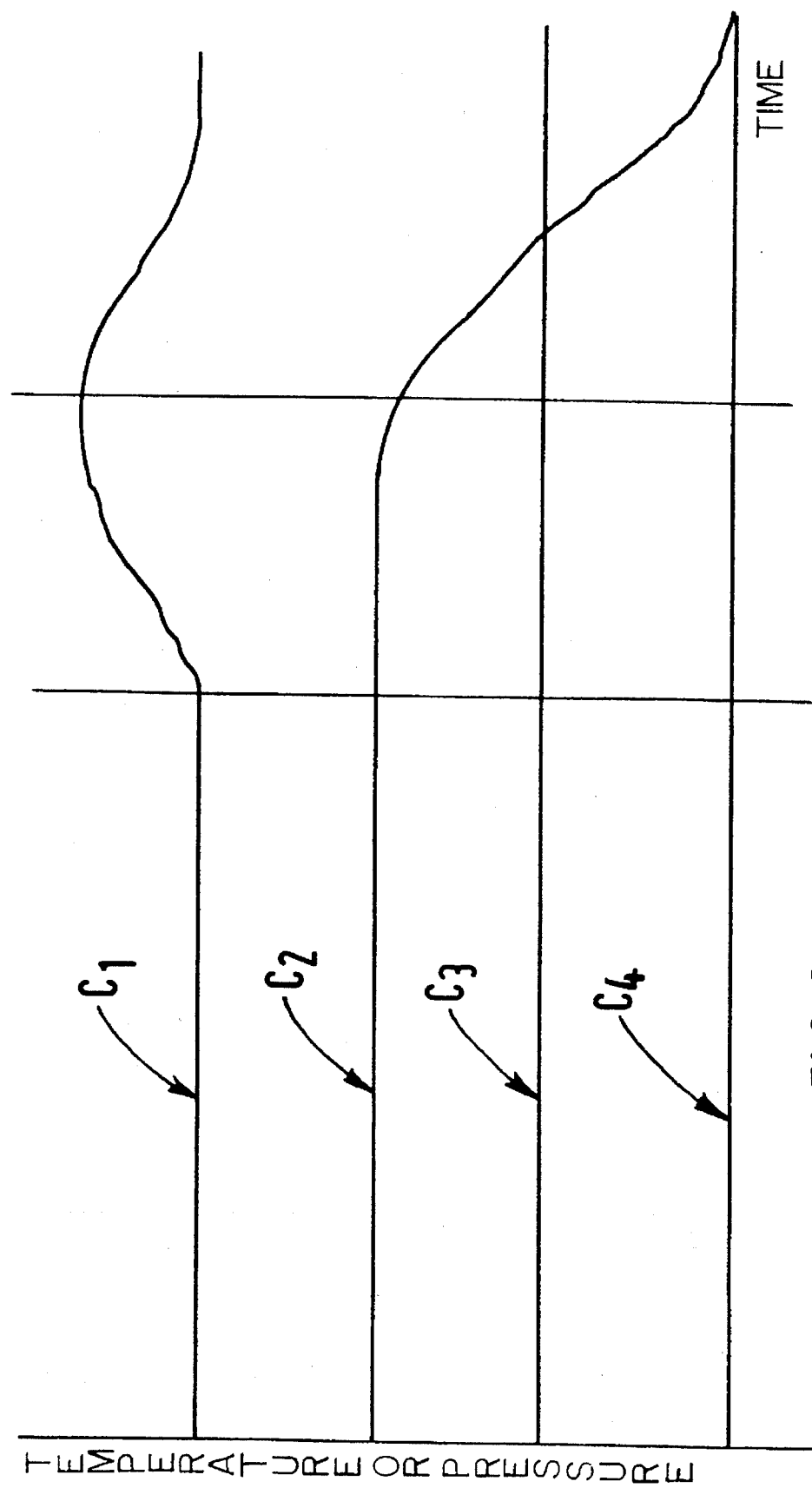
FIG. 2 is a graph of the curves recorded using an apparatus of this kind.
Figure 3:
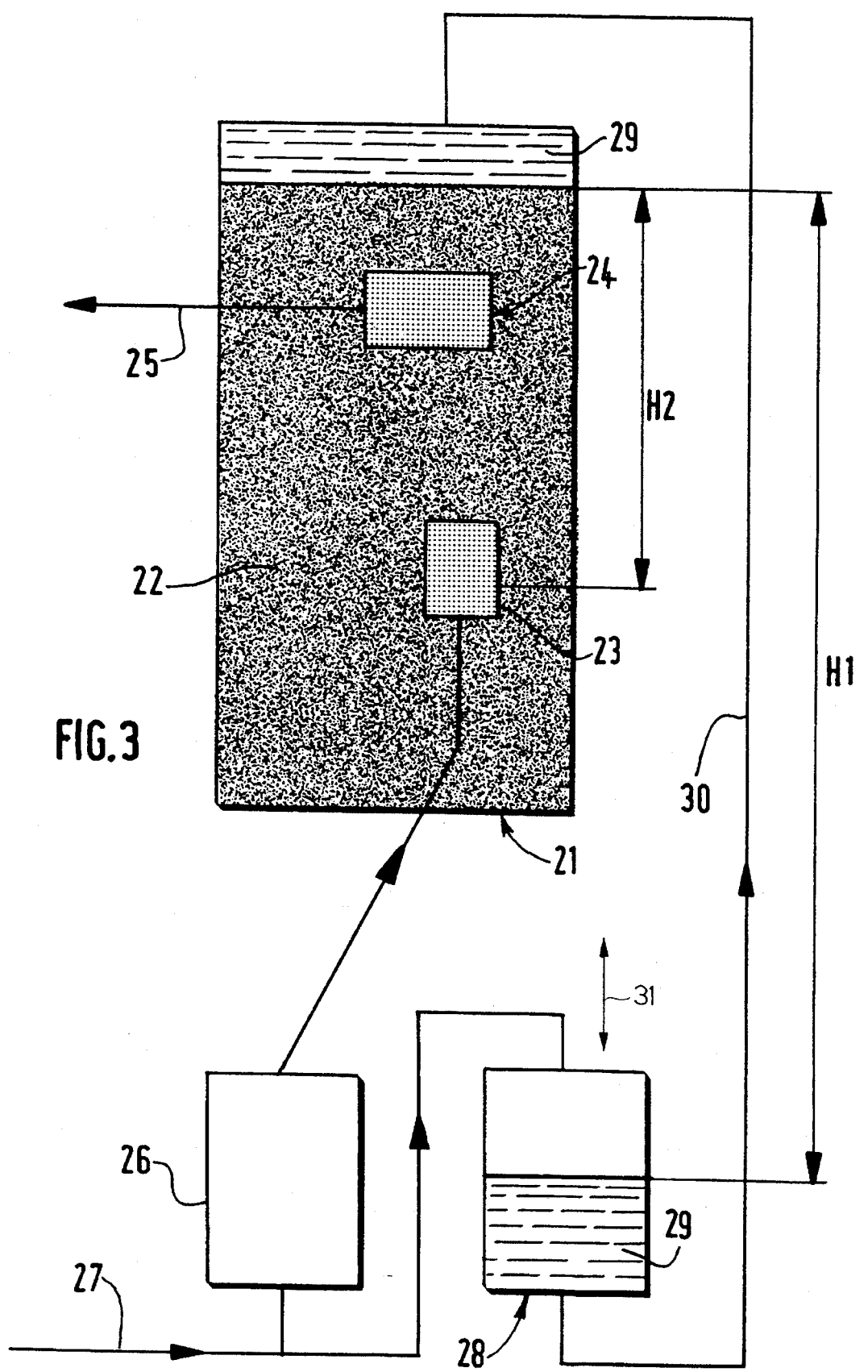
FIG. 3 is a graphic representation of an apparatus according to the invention.

The apparatus, its mode of use and the advantages thereof will now be described in greater detail with reference to the schematic drawing in FIG. 3, which illustrates a small cylindrical cell 21, e.g., having a height of 50 cm and a diameter of 5.4 cm. These dimensions make it possible to place it easily, if necessary, in a high-temperature oven, the components outside the cell being positioned outside the oven. This cell is designed to contain a cement slag 22, whose cementation one wishes to test in the laboratory.

A first, or injection, strainer 23 and a second, or detection, strainer 24 are housed in the cell 21 so as to be embedded in the cement. The strainer 24 is positioned at a level higher than that of the strainer 23, and is connected by a line 25 to gas-detection means (not shown/conventional). The strainer 23 is connected to a pressure-stabilization tank 26, which is, in turn, fed through a line 27 with a pressurized gas from a source (not shown).

The strainers 23 and 24 are composed of a hollow cylinder made of a porous sintered material, or a filter, natural rock, or compacted powder possessing stable permeability. The strainer 23 is arranged vertically, while the strainer 24 is arranged horizontally so that any liquid filtrate flowing into its hallow interior cannot accumulate therein, and disrupt the gas detection, but can instead be drained away naturally by gravity to the outside through the line 25.

At a level lower than that of the strainer 23, a tank 28 partially filled with water 29 is also fed in its upper part with pressurized gas flowing through the line 27. The lower part of this tank 29 is connected by means of a line 30 to the upper part of the cell 21, so that water 29 is present above the slag 22 and transmits to it the pressure of the gas.

The distance between the water-gas interface in the tank 28 and the water-slag interface in the cell 21 is marked with reference $H_1$ on the drawing, while the distance between the water-slag interface and the injection strainer 23 is referenced as $H_2$.

In operation, the gas-feed pressure $P_1$ from the tank 28 is generated at the water-gas interface. At the water-slag-interface in the cell, the pressure is equal to $P_1$, reduced by the pressure of a column of water (density d=1) having height $H_1$ expressed in millimeters, i.e., $P_1$–g H1/10, where g designates the acceleration constant of gravity.

Within the cell 21 at the level of the strainer 23, the pressure $P_2$ is thus equal to the pressure existing at the level of the water-slag interface, increased by the hydrostatic pressure of the slag column having height $H_2$ and density $d_1$, or:

$$P_2 = P_1 - g\frac{H1}{10} + g\frac{H2}{10} \times d_1$$

or:

$$P_2 = P_1 - \frac{g}{10}(H_1 - d_1 H_2).$$

Inside the injection strainer 23, the pressure is virtually equal to the gas-injection pressure $P_1$, if the hydrostatic pressure of the gas is ignored, and the differential pressure between the inside and the outside of the strainer, $P_1 - P_2$, is thus equal to g/10 ($d_1 H_2 - H_1$). This differential pressure corresponds to the losses of head occurring through the strainer.

As explained above, during the cement-hardening phase the hydrostatic pressure in the slag decreases. However, as long as the pressure outside of the strainer 23 remains higher than that existing inside the strainer, the injected gas cannot migrate through the slag.

This migration can potentially occur only beginning as of the moment when the differential pressure in the strainer is nil, i.e., when $d_1 H_2 - H_1 = 0$, i.e., when $d_1 = H1/H2$. Thus, it is clear that by modifying $H_1$, i.e., the height of the gas-water interface in the tank, it is possible to simulate an entire range of pressures generated by the formation fluids having equivalent densities $$d = \frac{H1}{H2}.$$

The height Hi is modified during testing to achieve the desired pressure range simulation by simply moving the tank 28 upwardly or downwardly using any suitable means, as indicated schematically by the arrow 31. It will be noted, in this regard, that a modification of the injection pressure $P_1$ of the gas does not change the differential pressure through the strainer 23.

The apparatus according to the invention is thus particularly simple as regards both its manufacture and its use. The volume of slag used is very small and is consistent with the standards of the American Petroleum Institute, thereby ensuring that the measurements made using this apparatus can be duplicated and that there will be a high degree of correlation with the other measurements carried out on the same slag formula (hardening time, rheology, filtration, etc.).

The test can be made completely automatic and can be recorded in the absence of any measures undertaken from the outside during the test.

The gas-feed pressure $P_1$ is established at the beginning of the test, thereby creating a containment pressure. As indicated, a variation of this pressure has no impact on the differential pressure at the level of the injection strainer, and, consequently, on the reliability of the measurements. Despite the very low values of the pressures generated (e.g., 0.2 to 1 bar, or 0.2 to $1 \times 10^5$ pascals), precise regulation of the gas-feed pressure $P_1$ is thus not necessary. The differential pressure is adjusted by modifying the height $H_1$ of the water column, and it thus lends itself to fixed, stable adjustment.

We claim:

1. An apparatus for studying gas migration during the cementation of a pipe in a well, said apparatus comprising:

a) a cell (21) adapted to be filled at least partially with a slag (22) to be used during cementation;

b) a first strainer (23) made of a sintered material which simulates a formation disposed at a first level in the cell;

c) a second strainer (24) made of a sintered material disposed in the cell at a second level higher than the first level, and connected to a gas-detection apparatus, the two levels at which the two strainers are positioned being such that they are embedded in the slag being studied;

d) a pressurized gas source (27) connected to the first strainer, and to a tank (28) partially filled with water (29), a water-gas interface in the tank being located at a level lower than that of the first strainer; and e) means (30) connecting a part of the tank (28) filled with water to an upper part of the cell, above an upper level of the slag (22).

2. An apparatus according to claim 1, wherein said strainers (23,24) each comprise a hollow body having stable permeability and made of one of a porous sintered material, a filter material, natural rock, and compacted powder.

3. An apparatus according to claim 2, wherein said second strainer (24) is arranged in the cell (21) in a position such that a filtrate which may flow therein will be carried away naturally by gravity to the outside.

4. An apparatus according to claim 3, wherein said second strainer is cylindrical and arranged horizontally.

* * * * *